United States Patent
Harichian et al.

(10) Patent No.: US 8,653,018 B2
(45) Date of Patent: Feb. 18, 2014

(54) FATTY ACYL AMIDO BASED SURFACTANT CONCENTRATES

(75) Inventors: Bijan Harichian, Brookfield, CT (US); Van Au, Oxford, CT (US); Badreddine Ahtchi-Ali, Newtown, CT (US); John Robert Winters, Dumont, NJ (US); Peter Anthony Divone, Sr., Shelton, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 131 days.

(21) Appl. No.: 13/192,492

(22) Filed: Jul. 28, 2011

(65) Prior Publication Data

US 2013/0030197 A1 Jan. 31, 2013

(51) Int. Cl.
*C11D 1/02* (2006.01)
*C11D 3/26* (2006.01)
*C11D 3/43* (2006.01)

(52) U.S. Cl.
USPC ........... 510/501; 510/136; 510/137; 510/138; 510/153; 510/505; 510/506

(58) Field of Classification Search
USPC .......... 510/136, 137, 138, 153, 501, 505, 506
See application file for complete search history.

(56) References Cited

U.S. PATENT DOCUMENTS

| | | | |
|---|---|---|---|
| 3,836,551 A | | 9/1974 | Schroeder et al. |
| 4,328,131 A * | | 5/1982 | Carson et al. .................. 510/145 |
| 4,812,253 A * | | 3/1989 | Small et al. .................... 510/151 |
| 5,154,849 A * | | 10/1992 | Visscher et al. ............. 510/150 |
| 5,194,639 A | | 3/1993 | Connor |
| 5,300,249 A * | | 4/1994 | Schwartz et al. ............. 510/153 |
| 5,529,712 A | | 6/1996 | Sano |
| 5,646,318 A | | 7/1997 | Dery |
| 5,705,462 A * | | 1/1998 | Hormes et al. ................. 510/141 |
| 5,710,295 A * | | 1/1998 | Woodbury et al. .............. 554/69 |
| 5,723,673 A | | 3/1998 | Kao |
| 5,767,059 A | | 6/1998 | Umemoto et al. |
| 6,395,692 B1 * | | 5/2002 | Jaworski et al. ............. 510/147 |
| 6,703,517 B2 | | 3/2004 | Hattori et al. |
| 6,958,085 B1 | | 10/2005 | Parrish |
| 7,439,388 B2 | | 10/2008 | Harichian et al. |
| 2001/0034311 A1* | | 10/2001 | Saxena et al. ................. 510/152 |
| 2002/0028954 A1 | | 3/2002 | Khoury et al. |
| 2004/0063980 A1 | | 4/2004 | Raths et al. |
| 2005/0176615 A1 | | 8/2005 | Kinoshita et al. |
| 2006/0090644 A1 | | 5/2006 | Sirkar |
| 2006/0239952 A1* | | 10/2006 | Hattori ........................ 424/70.14 |
| 2010/0029528 A1* | | 2/2010 | Giles et al. .................... 510/123 |

FOREIGN PATENT DOCUMENTS

| | | |
|---|---|---|
| DE | 2004099 | 1/1970 |
| DE | 4408957 A1 | 3/1994 |
| EP | 1801194 A1 | 6/2007 |
| GB | 1337782 | 11/1973 |
| JP | 5758653 | 9/1980 |
| WO | WO2008019807 A1 | 2/2008 |

OTHER PUBLICATIONS

Co-Pending U.S. Appl. No. 13/192,489, filed Jul. 28, 3011; titled Method for Preparing Fatty Acyl Amico Carboxylic Acid Based Surfactants.
Co-Pending U.S. Appl. No. 13/192,490, filed Jul. 28, 2011; titled General Mehtod for Preparing Fatty Acyl Amido Based Surfactants.
Co-Pending U.S. Appl. No. 61/512,434, filed Jul. 28, 2011; titled Concentrated Fatty Acyl Amido Surfactant Compositions.
Co-pending U.S. Appl. No. 13/343,731; filed Jan. 5, 2012.
Chen et al., Vinyl Carboxylate an Acylating Reagent for Selective Acylation Aminea and Dials, Tetrahedron Letters, 1994, vol. 35 No. 21, pp. 3583-3584.
Falk et al., The Preparation and Properties of Surface-Active N-Acylamino-Methanesulfonates, Journal of America Oil Chem Society, Apr. 1958, vol. 35 No. 4, pp. 171-176.
Martin et al., Application of AlMe3-Mediated Reaction to Solution Phase Peptide Synthesis, Tetrahedron Letters, 1998, vol. 39, pp. 1517-1520.
PCT International Search Report in PCT application PCT/EP2012/064772 dated Dec. 11, 2012 with Written Opinion.
PCT International Search Report in PCT application PCT/EP2012/064769 dated Dec. 7, 2012 with Written Opinion.
PCT International Search Report in PCT application PCT/EP2012./064771 dated Dec. 10, 2012 with Written Opinion.
PCT International Search Report in PCT application PCT/EP2012/064770 dated Dec. 10, 2012 with Written Opinion.
PCT International Search Report in PCT application PCT/EP2012/064768 dated Nov. 7, 2012 with Written Opinion.
Co-pending Application: Applicant: Harichian et al., U.S. Appl. No. 13/343,726, filed Jan. 5, 2012.
Co-pending Application: Applicant: Harichian et al., U.S. Appl. No. 13/343,727, filed Jan. 5, 2012.
Co-pending Applicant: Applicant: Harichian et al., U.S. Appl. No. 13/343,728, filed Jan. 5, 2012.
Co-pending Application: Applicant: Harichian et al., U.S. Appl. No. 13/343,730, filed Jan. 5, 2012.

* cited by examiner

*Primary Examiner* — Gregory Delcotto
(74) *Attorney, Agent, or Firm* — Karen E. Klumas

(57) ABSTRACT

A surfactant concentrate is provided that includes $C_8$-$C_{22}$ acyl amido compounds, a polyol and $C_8$-$C_{22}$ fatty acids. The concentrate is formed via an interesterification reaction between a $C_1$-$C_3$ alkyl ester of a $C_8$-$C_{22}$ fatty acid and an amino compound or salt thereof in a polyol. The resultant surfactant concentrate will have a Hunter Lab Color Scale value L ranging from 70 to 100.

12 Claims, No Drawings

FATTY ACYL AMIDO BASED SURFACTANT CONCENTRATES

BACKGROUND OF THE INVENTION

1. Field of the Invention

The invention concerns fatty acyl amido based surfactant concentrates.

2. The Related Art

Fatty acyl amido salts are desirable surfactants. They have good water solubility, good detergency and foaming properties. Most especially they are mild to the skin. Unfortunately the amount of and extent of their usage is limited because they are expensive to produce.

The most traditional and present commercial route to fatty acyl amido carboxylic salts is found in U.S. Pat. No. 6,703,517 (Hattori et al.). Synthesis is achieved by reacting the amino acid with activated fatty acid derivatives, especially fatty acyl chlorides. The process requires a mole equivalent of alkali to remove the hydrogen chloride byproduct of the reaction. There are evident waste disposal issues with the byproducts and the added cost of chloride is not fully recoverable. A still further problem is incompatibility of unsaturated fatty acids with the harsh reaction conditions. Unsaturates decompose and can form color bodies.

Direct esterification and interesterification are routes which also have been previously investigated. US Patent Application Publication No. 2006/0239952 A1 (Hattori) describes a reaction between a neutral amino acid and a long chain fatty acid catalyzed by an alkaline substance such as sodium hydroxide or potassium hydroxide. For instance, the reaction between glycine and lauric acid produces the acylated products lauroylglycine and lauroylglycylglycine. Significant byproducts include the non-acylated forms such as glycylglycine and glycyldiketopiperazine, as well as unreacted glycine. The reaction is said to be highly efficient (yield of the acylated forms) but this results because the ratio of lauric acid starting material to glycine is extremely high.

DE 44 08 957 A1 (BASF AG) reports N-acyl aminocarboxylic acids prepared by reaction of a suspension of solid anhydrous alkali metal salts of aminocarboxylic acids and an appropriate carboxylic acid or ester. Catalytic amounts of strong base are added to the suspension to promote the reaction. Illustrative is the reaction of equimolar amounts of lauric acid and anhydrous sodium sarcosine heated together molten at 200° C. in the presence of a molar equivalent of sodium hydroxide. Although the yields are high, the resultant product is highly colored.

None of the known esterification or interesterification processes are without a disadvantage. Many require relatively high temperatures and/or strong alkali to progress the reaction. These conditions promote side reactions of the amino acids with themselves rather than with the fatty acylating reagent. These competing reactions squander expensive amino acid starting reagent and require removal cleanup steps. Yields are also adversely affected. Furthermore, the necessary conditions for reaction in the known art are too harsh for the simpler amino acids.

A problem common to most acyl amido compounds produced by the known methods is discoloration of the reaction resultant concentrate. Small amounts of colored byproducts have significant visual impact.

SUMMARY OF THE INVENTION

A concentrate of $C_8$-$C_{22}$ acyl amido compounds is provided prepared by a process which includes:
(i) reacting an amino compound or salt thereof having a structure (I) with a $C_1$-$C_3$ alkyl ester of a $C_8$-$C_{22}$ fatty acid in a polyol medium,

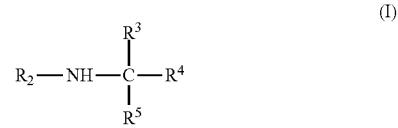

wherein $R^2$ is hydrogen or a $C_1$-$C_5$ alkyl radical; $R^3$ is hydrogen; $R^4$ is selected from the group consisting of $(CH_2)_mCO_2X$, $(CH_2)_mSO_3X$ and glucosyl radicals; $R^5$ is selected from the group consisting of hydrogen, hydroxyphenyl, $C_1$-$C_6$ hydroxyalkyl, $C_1$-$C_{10}$ alkyl, benzyl, hydroxybenzyl, alkylcarbamido, thioalkyl, and carboxylic radicals; X is selected from hydrogen, metal ions and $C_1$-$C_4$ alkyl radicals; and m ranges from 0 to 6; and (ii) heating reactants from step (i) to form the $C_8$-$C_{22}$ acyl amido compounds having a structure (II) and recovering a concentrate from the process

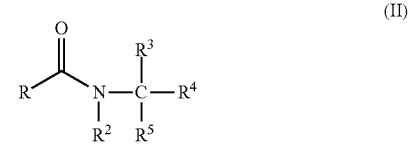

wherein R is a $C_7$-$C_{21}$ saturated or unsaturated alkyl radical; and the concentrate having a Hunter Lab Color Scale value L ranging from 70 to 100, the concentrate including:
a) from 40 to 90% by weight of $C_8$-$C_{22}$ acyl amido compounds of structure (II);
b) from 10 to 60% by weight of polyol; and
c) from 1 to 20% by weight of $C_8$-$C_{22}$ fatty acids.

DETAILED DESCRIPTION OF THE INVENTION

In our efforts to find an improved synthesis of C8-C22 acyl amido carboxylates and sulfonates, we have discovered that the resultant reaction masses are without further workup excellent surfactant concentrates. Now we can obtain foaming surfactant concentrates based on $C_8$-$C_{22}$ acyl amido carboxylic or sulfonic acids or salts thereof, in combination with polyol and fatty acids. These concentrates are relatively free of byproduct forming color bodies. The concentrate can be used as a cleanser per se or incorporated (dissolved or suspended) in an aqueous or non-aqueous liquid or bar with other formulation ingredients.

The concentrates have become available because of a relatively mild interesterification reaction that has achieved good yields of a surfactant active. An important element in both the interesterification reaction and the resultant concentrate product is that of a significant polyol presence.

Accordingly, concentrates of the present invention will contain $C_8$-$C_{22}$ acyl amido compounds of structure (II) in amounts ranging from 40 to 90%, preferably from 45 to 80%, and optimally from 50 to 75% by weight of the concentrate.

A polyol will also be present both in the concentrate and as a reaction medium for the interesterification leading to the concentrate. Illustrative polyols are glycerol, propylene glycol, dipropylene glycol, pentylene glycol, butylene glycol, isobutylene glycol and combinations thereof. Most preferred are glycerol and propylene glycol. Amounts of the polyol in the concentrate may range from 10 to 60%, preferably from 20 to 50%, and optimally from 25 to 45% by weight.

Another material present in the concentrate is $C_8$-$C_{22}$ fatty acids. Illustrative fatty acids include lauric, myristic, palmitic, stearic, oleic, linoleic, behenic acids and combinations thereof. Amounts of the fatty acids in the concentrate may range from about 1 to about 20%, preferably from 2 to 15%, and optimally from 4 to 10% by weight.

The concentrates of the present invention are made by the interesterification reaction schematically detailed below with glycerol representing the polyol reaction medium.

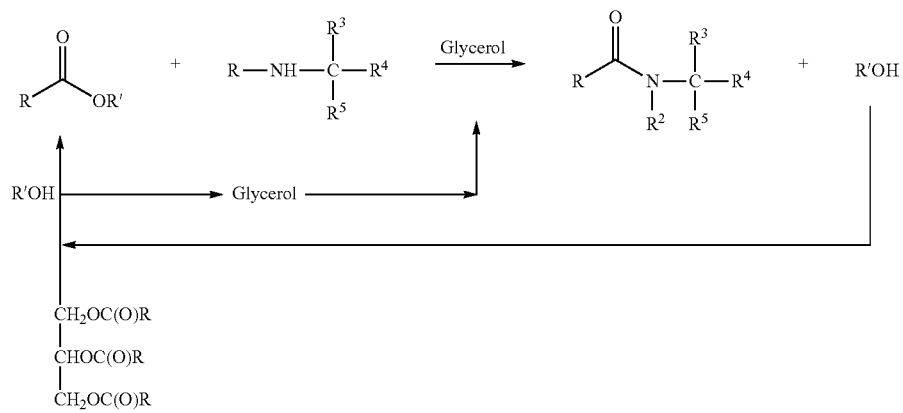

wherein R is a $C_7$-$C_{21}$ saturated or unsaturated alkyl radical; $R^1$ is a $C_1$-$C_4$ alkyl; $R^2$ is hydrogen or a $C_1$-$C_5$ alkyl radical; $R^3$ is hydrogen; $R^4$ is selected from the group consisting of $(CH_2)_mCO_2X$, $(CH_2)_mSO_3X$ and glucosyl radicals; $R^5$ is selected from the group consisting of hydrogen, hydroxyphenyl, $C_1$-$C_6$ hydroxyalkyl, $C_1$-$C_{10}$ alkyl, benzyl, hydroxybenzyl, alkylcarbamido, thioalkyl, and carboxylic radicals; X is selected from hydrogen, metal ions, amine salts and $C_1$-$C_4$ alkyl radicals; and m ranges from 0 to 6.

Salts of the amido carboxylic or sulphonic acid products of the process may have any type of cationic counterion X, but preferably are selected from sodium, potassium or mixed cations. Particularly suitable as the $R^1$ group is a methyl radical.

Advantageously, the reaction medium and resultant concentrate may be substantially free of water. By substantially free of water is meant amounts from 0 to 10%, preferably from 0 to 5%, more preferably from 0 to 3%, still more preferably from 0 to 1%, and especially from 0.05 to 1% by weight of water. Water of hydration (such as found associated with the amino carboxylic or sulphonic acid monohydrate) is not considered to count as part of water present in the reaction medium.

The reaction mixture desirably should have a pKa at 25° C. ranging from 9.5 to 13, and preferably from 10.5 to 12.

A first reagent is that of an amino compound or amino acid or salt thereof. Suitable salts include sodium and potassium salts, especially of the amino acids. The reagent may either be in an anhydrous or hydrated form.

Suitable amino compounds or salts thereof are those selected from the group consisting of alanine, valine, leucine, isoleucine, phenylalanine, tryptophan, methionine, proline, aspartic acid, glutamine acid, glycine, serine, threonine, cysteine, tyrosine, asparagines, glutamine, lysine, arginine, histidine, sarcosine, n-methylglucamine, glucamine and taurine. Particularly preferred are glycine, sarcosine, taurine, N-methylglucamine and glucamine.

A variety of esters may be suitable as co-reactants. Suitable esters include the $C_1$-$C_3$ alkyl esters of $C_8$-$C_{22}$ fatty acids. Illustrative are methyllaurate, methyloleate, methylinoleate, methylmyristate, methylstearate, methylpalmitate, ethyllaurate, ethyloleate, ethyllinoleate, ethylmyristate, ethylstearate, ethylpalmitate, n-propyllaurate, n-propyloleate, n-propyllinoleate, isopropyllaurate, isopropyloleate, isopropyllinoleate, isopropylmyristate, isopropylstearate, isopropylpalmitate and mixtures thereof. Particularly suitable is methyl cocoate.

The $C_1$-$C_3$ alkyl esters of $C_5$-$C_{22}$ fatty acids may be generated from triglycerides by hydrolysis with a respective $C_1$-$C_3$ alkanol. Most suitable as the alkanol is methanol. Amongst useful triglycerides are coconut oil, palm kernel oil, soybean oil, cottonseed oil, rapeseed oil, canola oil and mixtures thereof. Most preferred is coconut oil.

An advantage of the concentrates as produced by the described process in contrast to the traditional Schotten-Bauman acyl halide route is that unsaturated fatty esters such as oleyl and linoleyl esters can be tolerated and their amides obtained. Normally unsaturated acids will undergo decomposition or generate color bodies in the known processes. Minimum byproducts are produced in the present process to achieve relatively white to no more colored than light tan concentrates. For instance, where glycine is the reactant, we have found no evidence of a glycylglycine or glycyldiketopiperazine. Neither are there any waste streams. As is evidenced from the reaction schematic above, when glycerol is the polyol, the glycerol liberated from the triglyceride can be utilized as a reaction medium. The alcohol (for instance methanol) that distills off from the main reaction can be fed back into the triglyceride hydrolysis reaction to form new methyl fatty acid ester.

Relative molar amounts of amino compound or salt thereof to fatty acid ester as reactants for the interesterification may range from about 2:1 to about 1:2, preferably from about 2:1 to about 1:1, more preferably from 1.3:1 to 1.05:1.

Polyols will serve as a reaction medium. The relative mole ratio of polyol to the amino compound or salt thereof for the reaction may range from about 8:1 to about 1:1, preferably from about 6:1 to about 1:1, and more preferably from about 2:1 to 1:1.

Temperature conditions for the reaction may range from about 50° C. to about 150° C., preferably from about 80° C. to about 140° C., and optimally from about 110° C. to about 130° C.

Basic metal salt containing catalysts may usefully be present to improve reaction speeds and conversion levels. Particularly useful are alkaline and alkaline earth metal containing hydroxides, phosphates, sulphates and oxides including calcium oxide, magnesium oxide, barium oxide, sodium oxide, potassium oxide, calcium hydroxide, magnesium hydroxide, calcium phosphate, magnesium phosphate and mixtures thereof. Most suitable are calcium oxide and magnesium oxide, with the former being preferred. Amounts of the basic metal salt catalyst may range from about 1 to about 20%, preferably from about 1 to about 10%, more preferably from about 1.5 to 5% by weight of starting amino compound present in the reaction.

Buffering compounds may also in some embodiments have utility to improve conversions and reaction times of the present invention. Suitable buffers include trisodium phosphate, disodium hydrogen phosphate, sodium citrate, sodium carbonate, sodium bicarbonate, sodium borate and mixtures thereof. Particularly useful is trisodium phosphate. Amounts of the buffer may range from about 1 to about 30% by weight of the amino compound or salt thereof present in the reaction. Preferably the amount is from about 5% to about 15% by weight of the starting amino compound or salt thereof present in the reaction.

Advantageously, distillation of the alkanol (e.g. methanol) can be done under atmospheric as well as reduced pressure conditions.

Acylamido compounds of the concentrate may be formed of radicals that are saturated, unsaturated or combinations thereof. Unsaturated varieties may exhibit Iodine Number Values ranging from 0.5 to 20, preferably from 1 to 10, optimally from 2 to 8.

Without any further purification, the reaction mass produces a concentrate whose components need not be separated but have been found commercially useful as a combination. Polyol and fatty acid in combination with the main product, $C_8$-$C_{22}$ acyl amido compounds, may as a concentrate be formulated directly into personal care products such as body washes, toilet bars, shampoos or even lotions.

Colored byproducts ordinarily generated in previously known routes to acyl amido carboxylic or sulphonic salts are avoided through the present process. Confirmation of the absence of colored species, for instance where glycine is a reactant, any glycylglycine and glycyldiketopiperazine has been established as not present through chromatography and/or mass spectroscopy analytical procedures. Yet, perhaps the best indicator of the clean nature of products formed in the process is the visual lack of dark coloration (e.g. absence of tan, brown, or even green/blue heretofore evident from other glycinate forming pathways). Subsequent to the heating step (ii), the hot liquid mass of reaction product bearing acyl amido carboxylic or sulphonic acid/salt product and polyol is removed from the reactor and forms a semi-solid. Color of this mass is evaluated by the Hunter Lab Color Scale. The mass which is a surfactant concentrate from the reaction can vary in color from white to slightly off-white. On the Hunter scale, the key parameter will be the L value which is a reflectance measure of brightness. L should range between 70 and 100, preferably from 75 to 100, optimally 90 to 100. Desirably, the b value can also be considered. The "b" may range from 0 to 20, preferably from 0 to 15, optimally from 0 to 3. Of less impact is the "a" value, which may range from −2 to 8, preferably −1 to 5, and optimally from 0 to 4. Values for the present invention were established by comparing the concentrate color (at the end of the process) with a Color Metric Converter available online at http://www.colorpro.com/info/tools/convert.htm.

All documents referred to herein, including all patents, patent applications, and printed publications, are hereby incorporated by reference in their entirety in this disclosure.

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

Except in the operating and comparative examples, or where otherwise explicitly indicated, all numbers in this description indicating amounts of material ought to be understood as modified by the word "about".

It should be noted that in specifying any range of concentration or amount, any particular upper concentration can be associated with any particular lower concentration or amount.

The following examples will more fully illustrate the embodiments of this invention. All parts, percentages and proportions referred to herein and in the appended claims are by weight unless otherwise illustrated.

EXAMPLE 1

Concentrates of sodium cocoylglycinate, as the surfactant component, were prepared by the following procedure. A 250 ml 3-neck glass reactor vessel was used to conduct a series of comparative experiments. A central neck was fitted with a stirring rod with Teflon® blade at one end and a motor for rotating the rod at a second end. A second neck of the reactor was fitted with a water-cooled condenser leading to a Dean-Stark trap for collecting methanol generated in the interesterification reaction. The third neck was fitted with a thermometer attached to a temperature control device. The reactor was externally heated in a glas-col heating mantle. In experiment 1, the reactor was charged with 25 g glycerol, 0.41 g calcium oxide, 17.5 g sodium glycine, and 39 g cocoyl methyl ester. Initially two phases were present in the reactor. The reactants were then heated at 120° C. for 2 hours under constant stirring and dry nitrogen. The reactor contents were then cooled to a point just above solidification and removed from the reactor. The resultant mass constituting the concentrate was a white colored paste. Analysis by liquid chromatography revealed an approximately 87% yield (based on starting glycine) of sodium cocoyl glycinate.

The concentrate contained 50.3% sodium cocoyl glycinate, 7.2% $C_8$-$C_{18}$ fatty acids, 34.1% glycerol, 1.6% glycine, less than 1.0% methyl cocoate, and the remainder calcium oxide and other minor materials.

Via liquid chromatography/mass spec analysis, the sodium cocoyl glycinate was shown to contain the following fatty acid chain length distribution based on % amounts in the total concentrate: 5.0% $C_8$, 3.8% $C_{10}$, 27.4% $C_{12}$, 9.7% $C_{14}$, 4.5% $C_{16}$ and 6.9% $C_{18}$. The $C_{18}$ glycinate was a mixture of stearic, oleic and linoleic isomers. The unsaturated $C_{18}$ compounds survived the reaction conditions in contrast to their absence under conditions of the alternate acyl chloride route.

A series of further experiments were conducted to evaluate the importance of pKa (reflective of catalyst and buffer), reaction times and temperatures. These experiments are recorded in Table I. Reactants and conditions are identical to experiment 1, except where otherwise indicated through footnotes for Table I.

TABLE I

| Experiment No. | Glycerol | Calcium Oxide | Buffer | Reaction Mixture pKa | Reaction Time (Hours) | Yield (%) | Temp. (° C.) | Hunter Lab Color Scale | | |
|---|---|---|---|---|---|---|---|---|---|---|
| | | | | | | | | L | a | b |
| 1 | Yes | Yes | None | 9.6 | 2 | 87 | 120 | 95.28 | 0.56 | 12.98 |
| 2 | Yes | Yes | Yes[1] | 9.6 | 2 | 95+ | 120 | 93.12 | −0.52 | 2.41 |
| 3 | Yes | Yes[2] | None | 9.6 | 2 | 95+ | 120 | 93.12 | −0.52 | 2.41 |
| 4 | Yes | None | None | 9.6 | 4-5 | 40-50 | 120-140 | 95.28 | 0.56 | 12.98 |
| 5 | None | None | None | 9.6 | 5 | <10 | 110-150 | 46.2 | 9.21 | 33.05 |
| 6 | None | Yes | None | 9.6 | 2 | <5 | 120 | 46.2 | 9.21 | 33.05 |
| 7 | None | Yes | Yes | 9.6 | 2 | <5 | 120 | 46.2 | 9.21 | 33.05 |
| 8 | Yes | Yes[3] | Yes | 9.6 | 2 | 75 | 120 | 93.12 | −0.52 | 2.41 |
| 9 | Yes | Yes[4] | Yes | 9.6 | 2 | 30-50 | 110-120 | 93.53 | −0.12 | 6.07 |
| 10 | Propylene Glycol[5] | Yes | None | 10.2 | 5 | 84 | 120 | 93.12 | −0.52 | 2.41 |
| 11 | Propylene Glycol[5] | Yes | Yes[6] | 9.8 | 5 | 94 | 120 | 93.12 | −0.52 | 2.41 |
| 12 | Yes | Yes | Yes | 9.74 | 2 | 89 | 120 | 93.12 | −0.52 | 2.41 |
| 13 | Yes | Yes | Yes | 7.6 | 2 | 0 | 120 | 68.93 | 12.44 | 36.72 |
| 14 | Yes | Yes | Yes | 7.7 | 2 | 0 | 120 | 69.00 | 12.50 | 37.00 |
| 15 | Yes | Yes | Yes | 8.9 | 2 | 0 | 120 | 69.10 | 12.60 | 37.01 |

[1]Trisodium phosphate at 1.5 g.;
[2]Doubled CaO to 0.82 g.;
[3]Magnesium oxide substitute for calcium oxide at 0.41 g.
[4]Zinc oxide replacement for calcium oxide at 0.41 g.;
[5]Propylene glycol replaced glycerol at 25 g.;
[6]Trisodium phosphate doubled to 3.0 g.

Experiment 5 demonstrates that in the absence of glycerol, hardly any sodium cocoyl glycinate is formed. Similar results are seen in experiments 6 and 7 where only catalyst is present to influence the reaction. From these experiments it is clear that the polyol medium is the crucial aspect in driving good yields.

Experiments 12-15 demonstrate that reactions run at a pKa lower than 9.5 do not result in any glycinate product. Zero yields were noted at pKa of 7.6, 7.7 and 8.9.

EXAMPLE 2

A series of experiments were conducted to evaluate concentrate formation in reaction mediums other than polyols. The experiments were run with reactants and conditions identical to experiment 1, except where otherwise indicated as footnotes to Table II.

Based on the results reported in Table II, it is evident that methanol, ethanol, isopropyl alcohol, toluene, isoamyl alcohol and water were ineffective in providing any reasonable yields of sodium cocoyl glycinate. Only polyols such as glycerol and propylene glycol were effective at driving the reactions to high yields and thereby forming the surfactant concentrates of this invention.

EXAMPLE 3

A set of experiments were conducted to evaluate whether amino acids other then glycine such as amino sulphonic acids and glucosyl amines would also be reactive in the process and form surfactant functional concentrates. The experiments were conducted with reactants and under conditions identical to experiment 1, except glycine was replaced by sarcosine, taurine, or N-methylglucamine.

TABLE II

| Experiment No. | Medium[7] | Calcium Oxide | Buffer | Reaction Mixture pKa | Reaction Time (Hours) | Temp. (° C.) | Yield (%) | Hunter Lab Color Scale | | |
|---|---|---|---|---|---|---|---|---|---|---|
| | | | | | | | | L | a | b |
| 16 | Methanol | Yes[8] | None | 9.6 | 2 | 120 | <5 | 93.39 | 2.01 | 24.30 |
| 17 | Ethanol | Yes | Yes | 9.6 | 4.5 | 80 | <5 | 93.39 | 2.01 | 24.30 |
| 18 | Isopropyl Alcohol | Yes | Yes | 9.6 | 5 | 90 | <5 | 93.39 | 2.01 | 24.30 |
| 19 | Toluene | Yes | None | 9.6 | 5 | 110 | <5 | 93.39 | 2.01 | 24.30 |
| 20 | Isoamyl Alcohol | Yes | Yes[9] | 9.6 | 5 | 120 | <5 | 93.39 | 2.01 | 24.30 |
| 21 | Water | Yes | None | 9.6 | 3-5 | 95-100 | <5 | 68.93 | 12.44 | 36.72 |

[7]Amount of the medium was 100 g.
[8]Doubled CaO to 0.82 g.
[9]Trisodium phosphate doubled to 3.0 g.

TABLE III

| Experiment No. | Amino Reactant | Glycerol | Calcium Oxide | Buffer | Reaction Mixture pKa | Reaction Time (Hours) | Yield (%) | Temp. (°C.) | Hunter Lab Color Scale | | |
|---|---|---|---|---|---|---|---|---|---|---|---|
| | | | | | | | | | L | a | b |
| 22 | Sarcosine | Yes | Yes | Yes | 9.6 | 2 | 55-65 | 120 | 76.75 | 5.24 | 53.64 |
| 23 | Taurine | Yes | Yes | Yes[1] | 9.7 | 2 | 95+ | 120 | 93.3 | −0.12 | 6.07 |
| 24 | N-methylglucamine | Yes | Yes | Yes | 9.6 | 2 | 92 | 120 | 92.14 | 4.4 | 32.75 |

Experiments 22 and 23 produced respectively good yields of sodium cocoylsarcosinate and sodium cocoyltaurate and their concentrates. Amides of N-methyl glucamine were also provided in good yields as detailed in Experiment 24.

EXAMPLE 4

Typical formulations wherein the concentrate can be utilized are reported under Table IV.

TABLE IV

| | Formula No. (Weight %) | | | | | |
|---|---|---|---|---|---|---|
| Component | 1 | 2 | 3 | 4 | 5 | 6 |
| Sodium Cocoyl Glycinate Concentrate[1] | 50 | 40 | 30 | 60 | 60 | 20 |
| Cocoamidopropyl Betaine (35% Active) | 2.0 | 2.0 | 2.0 | — | 2.0 | 3.0 |
| Sunflower Seed Oil | 2.0 | 1.0 | — | 1.0 | — | 0.5 |
| Guar Hydroxypropyl Trimonium Chloride | 1.0 | 1.0 | 1.0 | — | 1.0 | 1.0 |
| Citric Acid | 0.5 | 0.5 | 0.5 | 0.5 | 0.5 | 0.5 |
| Fragrance | 1.0 | 1.0 | 1.0 | 1.0 | 1.0 | 1.0 |
| Preservative | 0.3 | 0.3 | 0.3 | 0.3 | 0.3 | 0.3 |
| Water | Bal | Bal | Bal | Bal | Bal | bal |

[1]Concentrate from Experiment No. 1.

Formulas Nos. 1 through 6 will exhibit good foaming properties. All the formulas are colored white or relatively colorless.

While the invention has been described in detail with reference to specific embodiments thereof, it will be apparent to one skilled in the art that various changes and modifications can be made therein without departing from the spirit and scope thereof.

What is claimed is:

1. A reaction mass concentrate of $C_8$-$C_{22}$ acyl amido compounds prepared by a process comprising:
   (i) reacting an amino compound or salt thereof having a structure (I) with a $C_1$-$C_3$ alkyl ester of a $C_8$-$C_{22}$ fatty acid in a polyol medium, wherein, at 25 degrees Celsius, a reaction mixture pKa of from 9.5 to 13 is provided,

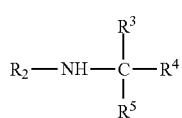

(I)

wherein $R^2$ is hydrogen or a $C_1$-$C_5$ alkyl radical; $R^3$ is hydrogen; $R^4$ is selected from the group consisting of $(CH_2)_mCO_2X$, $(CH_2)_mSO_3X$ and glucosyl radicals; $R^5$ is selected from the group consisting of hydrogen, hydroxyphenyl, $C_1$-$C_6$ hydroxyalkyl, $C_1$-$C_{10}$ alkyl, benzyl, hydroxybenzyl, alkylcarbamido, thioalkyl, and carboxylic radicals; X is selected from hydrogen, metal ions, amine salts and $C_1$-$C_4$ alkyl radicals; and m ranges from 0 to 6; and
   (ii) heating reactants from step (i) to form the $C_8$-$C_{22}$ acyl amido compounds having a structure (II)

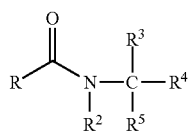

(II)

wherein R is a $C_7$-$C_{21}$ saturated or unsaturated alkyl radical; and
   (iii) recovering a reaction mass concentrate that, without further workup, has a Hunter Lab Color Scale value L ranging from 75 to 100, the concentrate comprising:
      a) from 40 to 90% by weight of $C_8$-$C_{22}$ acyl amido compounds of structure (II);
      b) from 10 to 60% by weight of polyol;
      c) from 1 to 20% by weight of $C_8$-$C_{22}$ fatty acids; and
      d) from 0 to 5% by weight of water,
wherein the polyol medium includes polyol selected from the group consisting of glycerol, propylene glycol, dipropylene glycol, pentylene glycol, butylene glycol, isobutylene glycol and combinations thereof.

2. The concentrate according to claim 1 wherein the ester is selected from the group consisting of methyllaurate, methyloleate, methylinoleate, methylmyristate, methylstearate, methylpalmitate, ethyllaurate, ethyloleate, ethylinoleate, ethylmyristate, ethylstearate, ethylpalmitate, n-propyllaurate, n-propyloleate, n-propyllinoleate, isopropyllaurate, isopropyloleate, isopropyllinoleate, isopropylmyristate, isopropylstearate, isopropylpalmitate and mixtures thereof.

3. The concentrate according to claim 1 wherein polyol is present in the concentrate in an amount of from 20 to 50% by weight.

4. The concentrate according to claim 1 wherein the polyol is selected from the group consisting of glycerol and propylene glycol.

5. The concentrate according to claim 1 wherein the acylamido compound has an Iodine Number Value ranging from 0.5 to 20.

6. The concentrate according to claim 1 wherein the amino compound or salt thereof is selected from the group consisting of alanine, valine, leucine, isoleucine, phenylalanine, tryptophan, methionine, proline, aspartic acid, glutamine acid, glycine, serine, threonine, cysteine, tyrosine, asparagines, glutamine, lysine, arginine, histidine, sarcosine, n-methylglucamine, glucamine and taurine.

7. The concentrate according to claim 1 wherein the amino compound or salt thereof is selected from the group consisting of glycine, sarcosine and taurine.

8. The concentrate according to claim 1 comprising from 0 to 3% water.

9. The concentrate according to claim 1 comprising from 0 to 1% water.

10. The concentrate according to claim 1 wherein the Hunter Lab Color Scale value L ranges from 90 to 100.

11. The concentrate according to claim 1 wherein the acyl amido compounds (II) include compounds having unsaturated groups R.

12. The concentrate according to claim 1 wherein polyol is present in the concentrate in an amount of from 25 to 45% by weight.

* * * * *